United States Patent [19]
Zöller et al.

[11] Patent Number: 5,951,982
[45] Date of Patent: Sep. 14, 1999

[54] METHODS TO SUPPRESS AN IMMUNE RESPONSE WITH VARIANT CD44-SPECIFIC ANTIBODIES

[75] Inventors: Margot Zöller, Heidelberg; Peter Herrlich, Karlsruhe; Helmut Ponta, Linkenheim-Hochstetten, all of Germany

[73] Assignee: Boehringer Ingelheim Pharmaceuticals, Inc., Ridgefield, Conn.

[21] Appl. No.: 08/359,850

[22] Filed: Dec. 20, 1994

Related U.S. Application Data

[63] Continuation of application No. 07/963,323, Oct. 23, 1992, abandoned.

[30] Foreign Application Priority Data

Oct. 23, 1991 [DE] Germany .............................. 41 34 982

[51] Int. Cl.⁶ .................... A61K 39/395; C07K 16/28
[52] U.S. Cl. .................... 424/154.1; 424/130.1; 424/131.1; 424/133.1; 424/136.1; 424/139.1; 424/141.1; 424/143.1; 424/144.1; 424/153.1; 530/387.1; 530/387.2; 530/387.3; 530/387.9; 530/388.1; 530/388.2; 530/388.22; 530/388.73; 530/388.75
[58] Field of Search .............................. 424/130.1, 131.1, 424/139.1, 138.1, 143.1, 144.1, 136.1, 152.1, 153.1, 154.1, 115.1, 156.1; 530/387.1, 387.7, 388.1, 388.22, 388.7, 388.73, 388.75, 388.8, 388.85, 387, 387.3, 387.9

[56] References Cited

FOREIGN PATENT DOCUMENTS

WO9117248  11/1991  WIPO.
9500658    1/1995   WIPO.

OTHER PUBLICATIONS

Weiss, J.M. et al., "An Essential Role for CD44 Variant Isoforms in Epidermal Langerhans Cell and Blood Dendritic Cell Function," *J. Cell. Biol.* 137:1137–1147 (Jun. 1997).
Tolg, C. et al., "Splicing Choice from Ten Variant Exons Establishes CD44 Variability," *Nucl. Acids Res.* 21:1225–1229 (1993).
Claas, C. et al., "Developmentally Regulated Expression of Metastasis–Associated Antigens in the Rat," *Cell Growth Differat.* 7: 663–678 (1996).
Sandmaier et al. Blood 91: 3494–3502 (1998).
Brennan Clin. Exp. Immunol. 97: 1–3 (1994).
Wittig et al. Immunology Letters 57: 217–223 (1997).
I. Albeldo Faseb J. 8: 504–512 (1994).
Cobbold et al., Nature 312?: 548–551 (1984).
Galuzzo et al. Eur. J. Immunol. 25: 2932–2939 Given at interview (#28) (1995).
Ward et al. Therapeutic Immunology 1: 165–171 (1994).
Zoller et al. Onkologie 17: 114–122 (1994).
Mountain et al. Biotech & Gen. Eng. Rev. 10: pp. 10–11 (1993).

Edgington et al. Biotechnology 10: 383–389 (1992).
Shaffer Biotechnology News Watch p. 9 Oct. 4, 1993.
Borre Breck et al. Immunol. Today 14: 477–479 (1993).
Joliffe Intern Rev. Immunol. 10: 241–50 (1993).
Koopman et al. J Exp Med 177: 897–904 (1993).
Harris et al. Tibtech 11: 42–44 (1993).
Waldmann Science 252: 1657–1662 (1991).
Vitetta et al. Ann. Rev. Immunol. 9: 193–217 (1991).
Hofmann et al. Cancer Res. 51: 5292–5297 (1991).
Stamenkovic et al. Embo J. 10: 343–348 (1991).
Neu, S., et al., "Expression Of CD44 Isoforms By Highly Enriched CD34–Positive Cells In Cord Blood, Bone Marrow And Leukaphereses," *Bone Marrow Transplantation,* 20:593–598 (1997).
Griffioen, A.W, et al., "Expression of CD44 Splice Variants During Lymphocyte Activation and Tumor Progression," *Cell Adhesion and Communication,* 2:195–200, (1994).
Levesque, M.C., et al., "In Vitro Culture Of Human Peripheral Blood Monocytes Induces Hyaluronan Binding And Up–Regulates Monocyte Variant CD44 Isoform Expression," *J. Immunol.* 156:1157–1565, (1996).
Pals, S.T., et al., "CD44 Splice Variants: Expression During Lymphocyte Activation and Tumor Progression," *Behring Inst. Mitt.,* 92:273–277 (1993).
Camp, R.L. et al., "High levels of CD44 expression distinguish virgin from antigen–primed B cells", *J. Exp. Med.* 173:763–766 (Mar. 1991).
Günthert, U. et al., "A new variant of glycoprotein CD44 confers metastatic potential to rat carcinoma cells", *Cell* 65:13–24 (Apr. 5, 1991).
Huet, S. et al., "CD44 contributes to T cell activation", *J. Immunol.* 143(3):798–801 (Aug. 1, 1989).
Jalkanen, S. et al., "Lymphocyte recognition of high endothelium: antibodies to distinct epitopes of an 85–95–kD glycoprotein antigen differentially inhibit lymphocyte binding to lymph node, mucosal, or synovial endothelial cells", *J. Cell Biol.* 105:983–990 (Aug. 1987).
Jalkanen, S.T. et al., "A lymphoid cell surface glycoprotein involved in endothelial cell recognition and lymphocyte homing in man", *Eur. J. Immunol.* 16:1195–1202 (1986).
Jerne, N.K. & Nordin, A.A., "Plaque formation in agar by singele antibody–producing cells", *Science* 140:405 (Apr. 26, 1963).
Matzku, S. et al., "Antigenic differences between metastatic and nonmetastatic BSp73 rat tumor variants characterized by monoclonal antibodies", *Cancer Research* 49:1294–1299 (Mar. 1, 1989).

(List continued on next page.)

Primary Examiner—Christina Y. Chan
Assistant Examiner—Phillip Gambel
Attorney, Agent, or Firm—Howrey & Simon; Jeffrey I Auerbach

[57] ABSTRACT

The present invention relates to a method of reducing or suppressing an immune response with antibodies specific for variants of the glycoprotein CD44. The invention further relates to a method of preventing or treating an immunoregulatory disorder or disease with these antibodies.

6 Claims, 10 Drawing Sheets

OTHER PUBLICATIONS

Reber, S. et al., "Retardation of metastatic tumor growth after immunization with metastatsis–specific monoclonal antibodies", *Int. J. Cancer 46*:919–927 (1990).

Shimizu, Y. et al., "Dual role of the CD44 molecule in T cell adhesion and activation", *J. Immunol. 143*(8):2457–2463 (Oct. 15, 1989).

Stamenkovic, I. et al., "A lymphocyte molecule implicated in lymph node homing is a member of the cartilage link protein family", *Cell 56*:1057–1062 (Mar. 24, 1989).

Zöller, M. & Andrighetto, G., "Comparison between the in Vitro activities of in Vivo–induced hapten–specific suppressor cells and supernatants of a hapten–specific suppressor hybridoma", *Cellul. Immunol. 89*:310–321 (1984).

Kavanaugh et al., Treatment of Refractory Rheumatoid Arthritis with Anti–CD54 Intercellular Adhesion Molecule–1 (ICAM–1) Monoclonal Antibody, Arthritis and Rheumatism, vol. 35.9, S43:53 (Sep. 1992).

Block 1 (position 599):

```
H:  E   D   S       W   T   D   F   F   N   P   I   S   H   P   M   G   R   H
    GAG GAC AGT     TCC ACT GAT TTC TTC AAC CCA ATC TCA CAC CCC ATG GGA CGA CAT
R:  E   D   V   S   W   T   D   F   F   D   P   I   S   H   P   M   G   Q   H
    GAG GAT GTT TCA TGG ACC GAT TTC TTC GAT CCA ATC TCA CAT CCA ATG GGA CAA CAT
```

Block 2 (position 659): ↓ DIV / M start

```
H:  Q   A   G   R   R   M   D   M       T   T   P   T   A
    CAA GCA GGA AGA AGG ATG GAC ATG     ACA ACG CCT ACT GCA
R:  Q   T   E   S   K       D           T   Q   L   P   T   A
    CAA ACA GAA AGC AAG     GAT         ACA CAG CTT CCT ACT GCG
```

Block 3 (position 719):

```
H:  N   P   N   T   T   G   D   L   R   T   G   P   L   S   M   T   T
    AAT CCA AAC ACA ACC CAT ... ...
R:  N   P   N   T   T   H   D   L   N   R   T   G   P   L   S   M   T   T
    AAT CCA AAC ACA ACC CAT GGC ... ...
```

Block 4 (position 779):

```
H:  Q   Q   S   N   S   F   S   Q   S   T   H   E   G   L   E   E   D   K   D
    CAG CAG AGT AAT TCT CAG AGC TTC TCT ACA TCA CAT GAA GGC TTG GAA GAT AAA GAC
R:  Q   Q   S   H   S   F   S   Q   N   F   T   L   P   G   E   L   E   E   D
    CCA CAG AGT CAT TCT CAG AAC TTC ... ACA TTA CCT GGA GAG CTG GAA GAA GAC
```

```
                                                                        D V
                                                                         ↓
H   H   P   T   T   S   T   L   T   S   N   R   N   D   V   G   R   R
H  CAT CCA ACA ACT ACT TCT ACT CTG ACA TCA AGC AAT AGG AAT GAT GTC ACA GGT GGA AGA AGA
R  CAT CCA ACA ACT ACT TCT GTT CTG CCA TCT AGC ACT AGC AAG AGT — — — — GGT CGA AGA AGA   839
                    P   T   V   L   P   S   S   T   S   K                G   R   R   R

H   D   P   N   H   H   S   E   G   S   T   L   L   E   G   Y   T   H   Y   P
H  GAC CCA AAT CAT CAT TCT GAA GGC TCA ACT TTA CTG GAA GGT TAT ACC CAT TAC CCA
R  GGT GGA AGT CTT CCC AGA GAT ACA ACT TCA GAA GGC TAC ACC CAA TAT CCA           899
    G   G   S   L   P   R   D   T   T   S   E   G   Y   T   Q   Y   P

H   T   K   E   S   R   T   F   I   P   V   S   A   K   T   G   S   F   G
H  ACG AAG GAA AGC AGG ACC TTC ATC CCA GTG TCA GCT AAG ACT GGG TCC TTT GGA
R  ACA ATG GAA AAC AGG ACT CTC TTC CCA GTG GCT GCT AAG ACT GAG GTC TTT GGA       959
    T   M   E   N   R   T   L   F   P   V   A   A   K   T   E   V   F   G

↓
H   V   T   A   V   T   G   —   G   D   S   N   N   V   N   R   S   L   S
H  GTT ACT GCA GTT ACT GTT —  — GGA GAT TCC AAC AAT GTC AAT CGT TCC TTA TCA G
R  GAA ACT GAA GGG ACT GCT GCT ACT GAC TCC AAC TCC AAC GTG GAT TCC TTA CCA G   1014
    E   T   E   G   T   A   A   T   D   S   N   S   N   V   D   S   L   P
```

FIG.4D

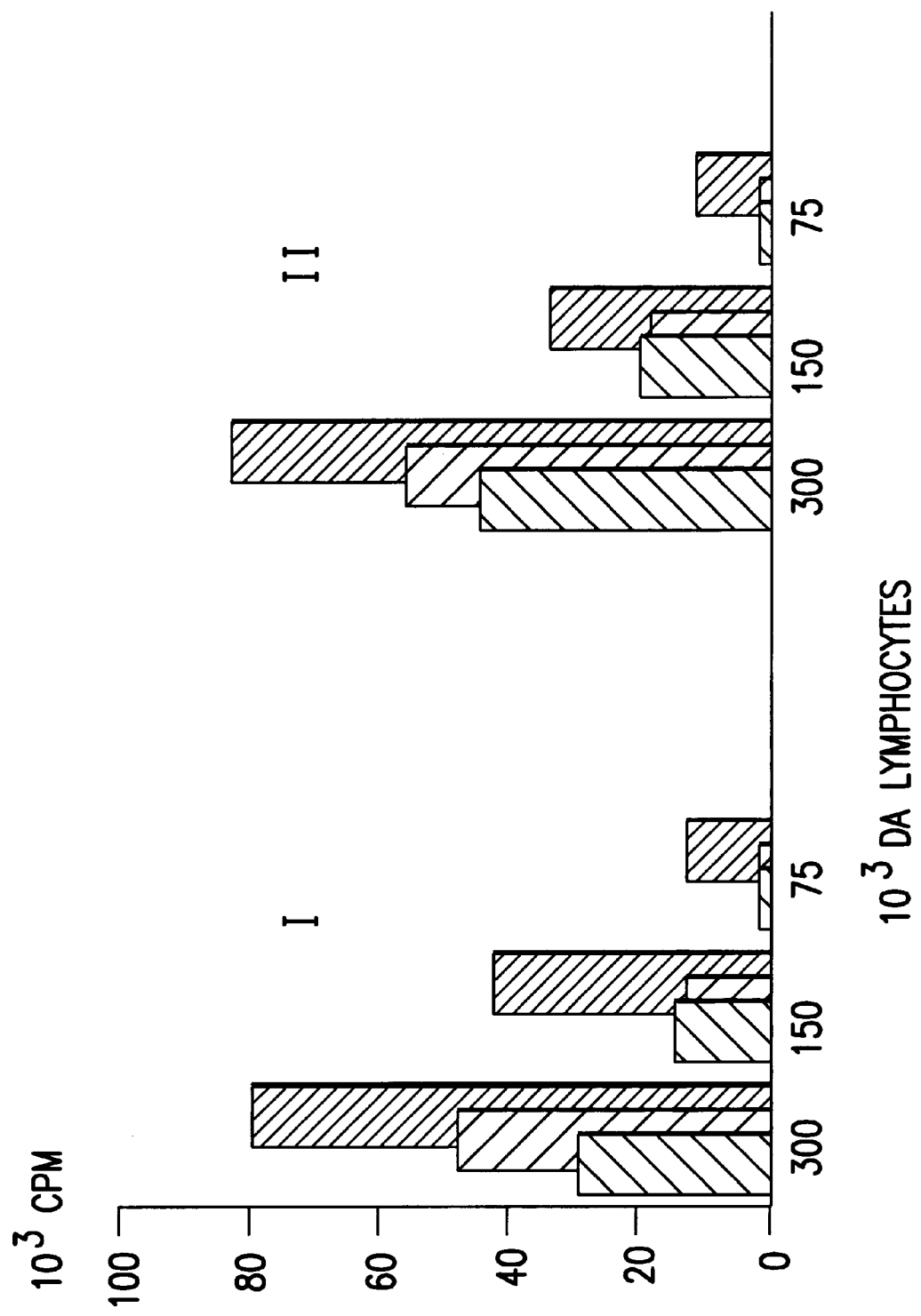

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 1014 base pairs
        (B) TYPE: nucleic acid
        (C) STRANDEDNESS: both
        (D) TOPOLOGY: linear (xi) SEQUENCE DESCRIPTION: SEQ ID NO:1:

```
GTACGTCTTC AAATACCATC TCAGCAGGCT GGGAGCCAAA TGAAGAAAAT GAAGATGAAA      60

GAGACAGACA CCTCAGTTTT TCTGGATCAG GCATTGATGA TGATGAAGAT TTTATCTCCA     120

GCACCATTTC AACCACACCA CGGGCCTTTG ACCACACAAA ACAGAACCAG GACTGGACCC     180

AGTGGAACCC AAGCCATTCA AATCCGGAAG TGCTACTTCA GACAACCACA AGGATGACTG     240

ATGTAGACAG AAATGGCACC ACTGCTTATG AAGGAAACTG GAACCCAGAA GCACACCCTC     300

CCCTCATTCA CCATGAGCAT CATGAGGAAG AAGAGACCCC ACATTCTACA AGCACAATCC     360

AGGCAACTCC TAGTAGTACA ACGGAAGAAA CAGCTACCCA GAAGGAACAG TGGTTTGGCA     420

ACAGATGGCA TGAGGGATAT CGCCAAACAC CCAGAGAAGA CTCCCATTCG ACAACAGGGA     480

CAGCTGCAGC CTCAGCTCAT ACCAGCCATC CAATGCAAGG AAGGACAACA CCAAGCCCAG     540

AGGACAGTTC CTGGACTGAT TTCTTCAACC CAATCTCACA CCCCATGGGA CGAGGTCATC     600

AAGCAGGAAG AAGGATGGAT ATGGACTCCA GTCATAGTAC AACGCTTCAG CCTACTGCAA     660

ATCCAAACAC AGGTTTGGTG GAAGATTTGG ACAGGACAGG ACCTCTTTCA ATGACAACGC     720

AGCAGAGTAA TTCTCAGAGC TTCTCTACAT CACATGAAGG CTTGGAAGAA GATAAAGACC     780

ATCCAACAAC TTCTACTCTG ACATCAAGCA ATAGGAATGA TGTCACAGGT GGAAGAAGAG     840

ACCCAAATCA TTCTGAAGGC TCAACTACTT TACTGGAAGG TTATACCTCT CATTACCCAC     900

ACACGAAGGA AGCAGGACC TTCATCCCAG TGACCTCAGC TAAGACTGGG TCCTTTGGAG      960

TTACTGCAGT TACTGTTGGA GATTCCAACT CTAATGTCAA TCGTTCCTTA TCAG          1014
```

(2) INFORMATION FOR SEQ ID NO:2:

(i) SEQUENCE CHARACTERISTICS:
        (A) LENGTH: 338 amino acids
        (B) TYPE: amino acid
        (D) TOPOLOGY: linear (xi) SEQUENCE DESCRIPTION: SEQ ID NO:2:

```
    Ser Thr Ser Ser Asn Thr Ile Ser Ala Gly Trp Glu Pro Asn Glu Glu
    1               5                   10                  15

Asn Glu Asp Glu Arg Asp Arg His Leu Ser Phe Ser Gly Ser Gly Ile
                    20                  25                  30

Asp Asp Asp Glu Asp Phe Ile Ser Ser Thr Ile Ser Thr Thr Pro Arg
                35                  40                  45

Ala Phe Asp His Thr Lys Gln Asn Gln Asp Trp Thr Gln Trp Asn Pro
            50                  55                  60

Ser His Ser Asn Pro Glu Val Leu Leu Gln Thr Thr Arg Met Thr
    65                  70                  75                  80

Asp Val Asp Arg Asn Gly Thr Thr Ala Tyr Glu Gly Asn Trp Asn Pro
                    85                  90                  95
```

```
Glu Ala His Pro Pro Leu Ile His His Glu His His Glu Glu Glu Glu
            100                 105                 110

Thr Pro His Ser Thr Ser Thr Ile Gln Ala Thr Pro Ser Ser Thr Thr
            115                 120                 125

Glu Glu Thr Ala Thr Gln Lys Glu Gln Trp Phe Gly Asn Arg Trp His
130                 135                 140

Glu Gly Tyr Arg Gln Thr Pro Arg Glu Asp Ser His Ser Thr Thr Gly
145                 150                 155                 160

Thr Ala Ala Ser Ala His Thr Ser His Pro Met Gln Gly Arg Thr
                165                 170                 175

Thr Pro Ser Pro Glu Asp Ser Ser Trp Thr Asp Phe Phe Asn Pro Ile
            180                 185                 190

Ser His Pro Met Gly Arg Gly His Gln Ala Gly Arg Arg Met Asp Met
        195                 200                 205

Asp Ser Ser His Ser Thr Thr Leu Gln Pro Thr Ala Asn Pro Asn Thr
210                 215                 220

Gly Leu Val Glu Asp Leu Asp Arg Thr Gly Pro Leu Ser Met Thr Thr
225                 230                 235                 240

Gln Gln Ser Asn Ser Gln Ser Phe Ser Thr Ser His Glu Gly Leu Glu
                245                 250                 255

Glu Asp Lys Asp His Pro Thr Thr Ser Thr Leu Thr Ser Ser Asn Arg
            260                 265                 270

Asn Asp Val Thr Gly Gly Arg Arg Asp Pro Asn His Ser Glu Gly Ser
            275                 280                 285

Thr Thr Leu Leu Glu Gly Tyr Thr Ser His Tyr Pro His Thr Lys Glu
290                 295                 300

Ser Arg Thr Phe Ile Pro Val Thr Ser Ala Lys Thr Gly Ser Phe Gly
305                 310                 315                 320

Val Thr Ala Val Thr Val Gly Asp Ser Asn Ser Asn Val Asn Arg Ser
                325                 330                 335

Leu Ser (2) INFORMATION FOR SEQ ID NO:3:

(i) SEQUENCE CHARACTERISTICS:
        (A) LENGTH: 1002 base pairs
        (B) TYPE: nucleic acid
        (C) STRANDEDNESS: both
        (D) TOPOLOGY: linear (xi) SEQUENCE DESCRIPTION: SEQ ID NO:3:

GTACGGAGTC AAATACCAAC CCAACAGGCT GGAAGCCAAA TGAGGAAAAT GAAGATGAAA        60

CAGACAAATA CCCCAATTTT TCTGGATCAG GCATTGATGA TGATGAAGAT TTTATCTCCA       120

GCACCATTGC AACTACTCCA TGGGTTTCTG CCCACACAAA ACAGAACCAG GAACGGACCC       180

AGTGGAACCC AATCCATTCA AACCCAGAAG TACTACTTCA GACAACCACC AGGATGACTG       240

ATATAGACAG AAACAGCACC AGTGCTCATG GAGAAAACTG GACCCAGGAA CCACAGCCTC       300

CTTTCAATAA CCATGAGTAT CAGGATGAAG AGGAGACCCC ACATGCTACA AGCACAACCT       360

GGGCAGATCC TAATAGCACA ACAGAAGAAG CAGCTACCCA GAAGGAGAAG TGGTTTGAGA       420

ATGAATGGCA GGGGAAGAAC CCACCCACCC CAAGTGAAGA CTCCCATGTG ACAGAAGGGA       480

CAACTGCCTC AGCCCACAAC AACCATCCAA GTCAAAGAAT GACAACACAG AGTCAAGAGG       540

ATGTTTCATG GACCGATTTC TTCGACCCAA TCTCACATCC AATGGGACAA GGTCATCAAA       600

CAGAAAGCAA GGATACAGGC TCCAGTCATA GTACAACCCT TCAGCCTACT GCGGCTCCAA       660
```

```
ATACCCATTT GGTGGAAGAC TTGAACAGGA CAGGACCACT TTCAGTGACA ACTCCACAGA    720

GTCATTCTCA GAACTTCTCT ACATTACCTG GAGAGCTGGA AGAAGGCGAA GACCATCCAA    780

CAACTTCTGT TCTGCCATCT AGCACTAAGA GTGGTCGAAG AAGAGGTGGA AGTCTTCCCA    840

GAGATACAAC TACTTCACTG GAAGGCTACA CCCCTCAATA TCCAGACACA ATGGAAAACG    900

GGACTCTCTT CCCAGTGACC CCTGCTAAGA CTGAGGTCTT TGGAGAAACT GAAGGGACTG    960

TTGCTACTGA CTCCAACTTT AATGTGGATG GCTCCTTACC AG                     1002
```

(2) INFORMATION FOR SEQ ID NO:4:

(i) SEQUENCE CHARACTERISTICS:
        (A) LENGTH: 334 amino acids
        (B) TYPE: amino acid
        (D) TOPOLOGY: linear (xi) SEQUENCE DESCRIPTION: SEQ ID NO:4:

```
Ser Thr Glu Ser Asn Thr Asn Pro Thr Gly Trp Lys Pro Asn Glu Glu
 1               5                  10                  15

Asn Glu Asp Glu Thr Asp Lys Tyr Pro Asn Phe Ser Gly Ser Gly Ile
            20                  25                  30

Asp Asp Asp Glu Asp Phe Ile Ser Ser Thr Ile Ala Thr Thr Pro Trp
        35                  40                  45

Val Ser Ala His Thr Lys Gln Asn Gln Glu Arg Thr Gln Trp Asn Pro
50                  55                  60

Ile His Ser Asn Pro Glu Val Leu Leu Gln Thr Thr Arg Met Thr
65                  70                  75                  80

Asp Ile Asp Arg Asn Ser Thr Ser Ala His Gly Glu Asn Trp Thr Gln
                85                  90                  95

Glu Pro Gln Pro Pro Phe Asn Asn His Glu Tyr Gln Asp Glu Glu
            100                 105                 110

Thr Pro His Ala Thr Ser Thr Thr Trp Ala Asp Pro Asn Ser Thr Thr
        115                 120                 125

Glu Glu Ala Ala Thr Gln Lys Glu Lys Trp Phe Glu Asn Glu Trp Gln
130                 135                 140

Gly Lys Asn Pro Pro Thr Pro Ser Glu Asp Ser His Val Thr Glu Gly
145                 150                 155                 160

Thr Thr Ala Ser Ala His Asn Asn His Pro Ser Gln Arg Met Thr Thr
                165                 170                 175

Gln Ser Gln Glu Asp Val Ser Trp Thr Asp Phe Phe Asp Pro Ile Ser
            180                 185                 190

His Pro Met Gly Gln Gly His Gln Thr Glu Ser Lys Asp Thr Gly Ser
        195                 200                 205

Ser His Ser Thr Thr Leu Gln Pro Thr Ala Ala Pro Asn Thr His Leu
210                 215                 220

Val Glu Asp Leu Asn Arg Thr Gly Pro Leu Ser Val Thr Thr Pro Gln
225                 230                 235                 240

Ser His Ser Gln Asn Phe Ser Thr Leu Pro Gly Glu Leu Glu Glu Gly
                245                 250                 255

Glu Asp His Pro Thr Thr Ser Val Leu Pro Ser Ser Thr Lys Ser Gly
            260                 265                 270

Arg Arg Arg Gly Gly Ser Leu Pro Arg Asp Thr Thr Thr Ser Leu Glu
        275                 280                 285

Gly Tyr Thr Pro Gln Tyr Pro Asp Thr Met Glu Asn Gly Thr Leu Phe
290                 295                 300

Pro Val Thr Pro Ala Lys Thr Glu Val Phe Gly Glu Thr Glu Gly Thr
```

```
                305                 310                 315                 320

Val Ala Thr Asp Ser Asn Phe Asn Val Asp Gly Ser Leu Pro
                    325                 330

(2) INFORMATION FOR SEQ ID NO:5:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO:5:

Glu Glu Ala Ala Thr Gln Lys Glu Lys Trp
    1               5                   10
```

METHODS TO SUPPRESS AN IMMUNE RESPONSE WITH VARIANT CD44-SPECIFIC ANTIBODIES

This application is a file-wrapper-continuation of U.S. Ser. No. 07/963,323, filed Oct. 23, 1992, now abandoned.

FIELD OF THE INVENTION

The present invention relates to the use of antibodies, particularly monoclonal antibodies, directed against variants of the glycoprotein CD44 (vCD44), for immunosuppression in mammals and in humans.

BACKGROUND INFORMATION

CD44 is a glycoprotein located on the cell surface which was originally described as a "lymphocyte homing receptor" and would appear to be implicated in the adhesion of lymphocytes to certain mucosal endothelial cells of veins (Peyer's patch or Peyer-Plaques or Folliculi lymphatici aggregati) or postcapillary veins in the lymph nodes (S. T. Jalkanen et al., *Eur. J. Immuol.* 16:1195–1202 (1986); R. L. Camp et al., *J. Exp. Med.* 173:763–766 (1991)). In addition, CD44 glycoprotein is thought to be implicated in the maturation and activation of lymphocytes and has a (co) determining effect on the increased migration capacity of all lymphoblasts (e.g. R. L. Camp et al. (1991) loc. cit; S. Huet et al., *J. Immunol.* 143:798–801 (1989)) and is believed to play a role as an anchor point for other adhesion molecules (Y. Shimizu et al., *J. Immunol.* 143:2457–2463 (1989)). However, as of the present, CD44 has not been clearly found to possess all these functions.

Recently, it was found, in experiments on rat tumor cells which metastasize via the lymphatic system (BSp73 cells of a spontaneous rat pancreas adenocarcinoma) that these cells express variants of CD44 (vCD44) and are responsible for the "trafficking" of tumor cells. This situation has also been demonstrated on other tumor cell lines.

It has been demonstrated that this vCD44 glycoprotein imparts metastasizing qualities to a tumor which, a prior, does not metastasize, whereas the standard type CD44 (sCD44) is not capable of this. Thus, it can now be assumed that vCD44 as opposed to CD44 is a metastasis-specific protein which enables tumors to metastasize through the lymph tracts (U. Günthert et al., *Cell* 65:13–24 (1991)).

Further clarification of the vCD44 glycoprotein of the rat up to the final characterization of the DNA and amino acid sequence was achieved by U. Günthert et al. (1991), loc. cit., by means of the BSp73 rat cell system which consists of two morphologically or phenotypically different syngeneic cell variants: a non-metastasizing variant AS (BSp73AS) and a metastasizing variant ASML (BSp73ASML) (S. Matzku et al., *Cancer Research* 49:1294–1299 (1989)).

For this purpose, monoclonal antibodies (mAbs) were prepared which recognize the antigenic determinant on the metastasizing variant BSp73ASML.

Cell lines have been obtained both from the primary tumor (subcutaneous non-metastasizing node consisting of BSp73AS cells) and also a metastasis thereof (BSp73ASML cells which metastasize in lymph nodes and lungs). mAbs were prepared which were directed against the membrane proteins of BSp73ASML cells (S. Matzku et al. (1989), loc. cit.). One of these mAbs, which recognizes only epitopes on BSp73ASML, but not those on BSp73AS cells or other non-tumorigenic cells, was used to search through an *E. coli* cDNA expression library, prepared from poly(A)$^+$RNA from BSp73ASML cells and a suitable vector system (screening). In this way it was possible to identify a clone (pMeta-1) which contains the total cDNA with a length of 3207 bp and which codes for an additional domain of 162 amino acids. This domain cannot be found either in sCD44 cells or in other non-metastasizing tumor cells and contains the mAb specific epitope-coding region. Using mRNA preparations from cells from various tissues and mRNA:DNA hybridizations carried out therewith, with different DNA samples obtained from the cDNA clones, the object was to establish that vCD44 is a splicing variant of sCD44 and that the expression of the vCD44 RNAs is closely linked to the formation of metastases. Thus, it is found that the additional extracellular domain coded by the 486 bp long insert (amino acids 224 to 385 in pMeta-1) is the part of the surface glycoprotein vCD44 which is implicated in metastasis.

The metastatic tumor growth (adenocarcinoma in the rat) was successfully suppressed after immunization with monoclonal antibodies which recognize the above-mentioned epitope or which specifically react with this extracellular region of vCD44 (S. Reber et al., *Int. J. Cancer* 46:919–927 (1990)).

The identification of this extracellular variant domain in the rat (pMeta-1 or rMeta-1) also makes it possible to clarify the equivalent human nucleotide and amino acid sequences:

Using a cDNA probe derived from the DNA of the vCD44 domain in the rat homologous regions in these DNAs can be found by hybridization, optionally under stringent conditions, with genomic DNA from various species-specific cell lines (e.g. human, rat, mouse). A probe of this kind can subsequently be used for hybridizing against RNAs from various human cell lines, especially tumor cell lines, e.g. large-cell lung cancers, melanomas, colon carcinomas, breast tumors, keratinocytes. In this way a suitable human cell line, e.g. that of a large-cell lung cancer, can readily be found containing sequences which are homologous to the cDNA probe of the rat. By PCR (polymerase chain reaction), a known in vitro method of selectively concentrating DNA regions of a specific length and specific sequence from a mixture of DNA molecules, using a DNA polymerase and a suitable primer, it is possible to obtain cDNAs from RNA preparations of various human cell lines, e.g. cells of large-cell lung cancers, melanomas, colon carcinomas and immortalized keratinocytes, which code for sCD44 and vCD44.

A cDNA of this kind obtained by PCR can be ligated into a suitable cloning vector by known methods and subsequently sequenced, after corresponding cultivation of the host cells transformed therewith, preferably bacteria such as *E. coli*. In this way, it is possible to obtain, from a variety of human cells selected from all possible tumor cells or cell lines, especially those which have metastasizing properties, DNA sequences which code either for a normal human sCD44 glycoprotein of a known order of magnitude in the region of 350 amino acids (I. Stamenkovic et al., *Cell* 56: 1057–1062 (1989)) which contains an extracellular domain in the region of 85 kDa (S. Jalkanen et al., *J. Cell Bol.* 105:983–990 (1987)) or which code for a variant human vCD44 glycoprotein which may comprise an additional extracellular domain of varying lengths, more particularly between 850 bp and 1.5 kb, for example 1014 bp (or 338 amino acids), and which is inserted in the DNA sequence coding for the normal sCD44 glycoprotein, for example between the positions of the nucleotides 782 and 783 (FIG. 4). A DNA sequence of this kind may occur in several, e.g. five domains which represent different exons and may be found both in various animal cell lines (e.g. the rat or mouse) and also in human cell lines.

The cDNA shown by way of example in FIG. 4A, which is homologous with the longest variant section of human tumor cell lines obtained, was isolated from the rat tumor cell line BSpASML using PCR. A direct comparison of the amino acid sequence derived therefrom with that of the human clone obtained from a human tumor cell line shows that domain I has 83%, domain II has 83%, domain III has 71%, domain IV has 82% and domain V has 66% homology with the rat DNA sequence. Overall this means that about 76% of the human sequences are conserved in the variant regions as compared with the rat sequence. The corresponding rat sequences which impart the metastatic potential to the tumor (U. Günthert et al. (1991), loc. cit.) comprise amino acids 258 to 420 and are coded by the domains II and III.

It was thus clear to those skilled in the art that poly- or monoclonal antibodies which specifically recognize these epitopes, i.e. this additional extracellular region on various splicing variants of vCD44 and react therewith, and which may be labelled with radioisotopes and/or conjugated with cytocidal or cytotoxic substances, may be used for diagnostic and therapeutic purposes in the treatment of metastasizing tumors in humans (see PCT WO 91/17248).

It has now, surprisingly, been found that antibodies, especially monoclonal antibodies which react with the various metastasis-specific variants of CD44 (vCD44) have an immunosuppressant activity; this new property could not have been foreseen under any circumstances in the light of the facts outlined above.

SUMMARY OF THE INVENTION

It is a general object of the invention to provide a method of reducing or suppressing an immune response.

It is a specific object of the invention to provide a method of reducing or suppressing an immune response in a mammal comprising administering to the mammal a variant CD44 (vCD44) antibody or fragment or derivative thereof under conditions such that the immune response is reduced or suppressed.

It is a specific object of the invention to provide a method of preventing an immunoregulatory disorder or disease comprising administering to the mammal a variant CD44 (vCD44) antibody or fragment or derivative thereof under conditions such that the disorder or disease is prevented.

It is a specific object of the invention to provide a method of treating an immunoregulatory disorder or disease comprising administering to the mammal a variant CD44 (vCD44) antibody or fragment or derivative thereof under conditions such that a symptom of the disorder or disease improves.

It is a specific object of the invention to provide a pharmaceutical composition comprising a variant CD44 (vCD44) antibody or fragment or derivative thereof in an amount effective to reduce or suppress an immune response in a mammal and a pharmaceutically acceptable diluent, carrier, or excipient.

It is a specific object of the invention to provide a pharmaceutical composition comprising a variant CD44 (vCD44) antibody or fragment or derivative thereof in an amount effective to treat an immunoregulatory disorder or disease and a pharmaceutically acceptable diluent, carrier, or excipient.

It is a specific object of the invention to provide a pharmaceutical composition comprising a variant CD44 (vCD44) antibody or fragment or derivative thereof in an amount effective to prevent an immunoregulatory disorder or disease and a pharmaceutically acceptable diluent, carrier, or excipient.

Further objects and advantages of the present invention will be clear from the description that follows.

BRIEF DESCRIPTION OF THE FIGURES

FIG. 5: Influence of anti-vCD44 (1.1ASML) on the allogenic activation of T-lymphocytes (measured as the incorporation of $^3$H-thymidine after stimulation=CPM). I=spleen cells, II=lymph node cells, both from DA rats. Immunization of the DA rats with BDX (lymphocytes irradiated with 3000R).

◻=Immunization with BDX, stimulated with BDX in vitro

Figure 6:
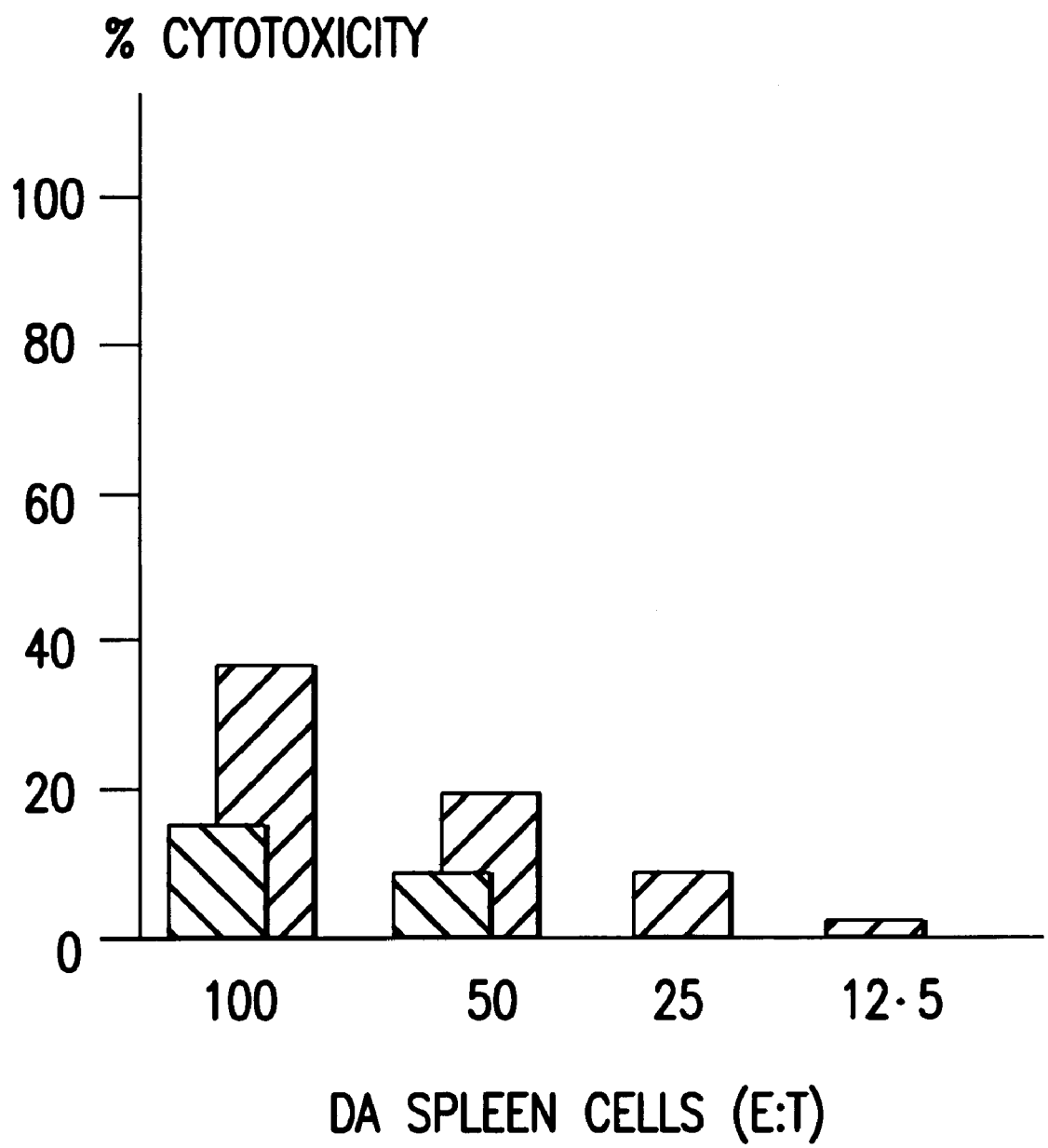

▨=Immunization with BDX in the presence of 1.1ASML, stimulated with BDX in vitro ◨=Immunization and stimulation with BDX in the presence of 1.1ASML FIG. 6: Influence of anti-vCD44 (1.1ASML) on the activation of cytotoxic T-cells, primary CTL. Immunization of DA rats with BDX (lymphocytes irradiated with 3000R).

▨=Immunization with BDX

▨=Immunization with BDX in the presence of 1.1ASML

E:T=Ratio of effector cells (E, spleen cells) to target cells (T, $^{51}$Cr-labelled BDX lymphoblasts).

DETAILED DESCRIPTION OF THE INVENTION

The invention therefore relates to the use of antibodies, particularly monoclonal antibodies, which react with metastasis-specific variants of CD44 (vCD44) in mammals, for producing preparations for generating a transient or lasting immunosuppression in mammals and in humans.

It should be emphasized at this point that every possible variant CD44 (vCD44) glycoprotein of animal or human origin and the nucleic acids (DNAs and RNAs) which code it and occur as inserts within the gene region coding for sCD44 are now available to those skilled in the art and it is within the capabilities of a person of ordinary skill in the art to use these proteins and the nucleic acids coding these proteins in order to prepare and use any desired antibodies, particularly monoclonal antibodies, fragments and derivatives thereof, for the purposes according to the invention.

Figure 4A:
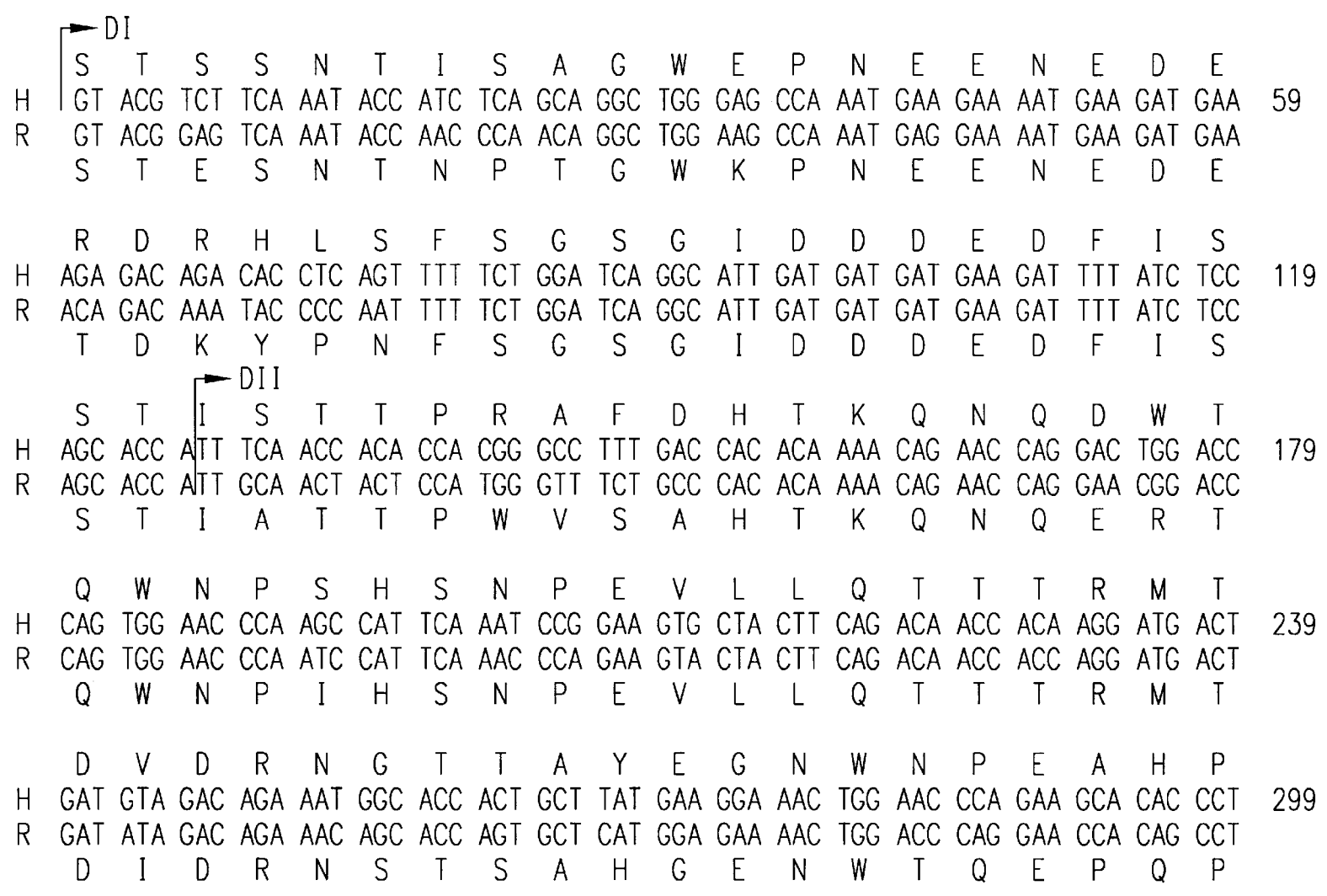
Figure 4B:
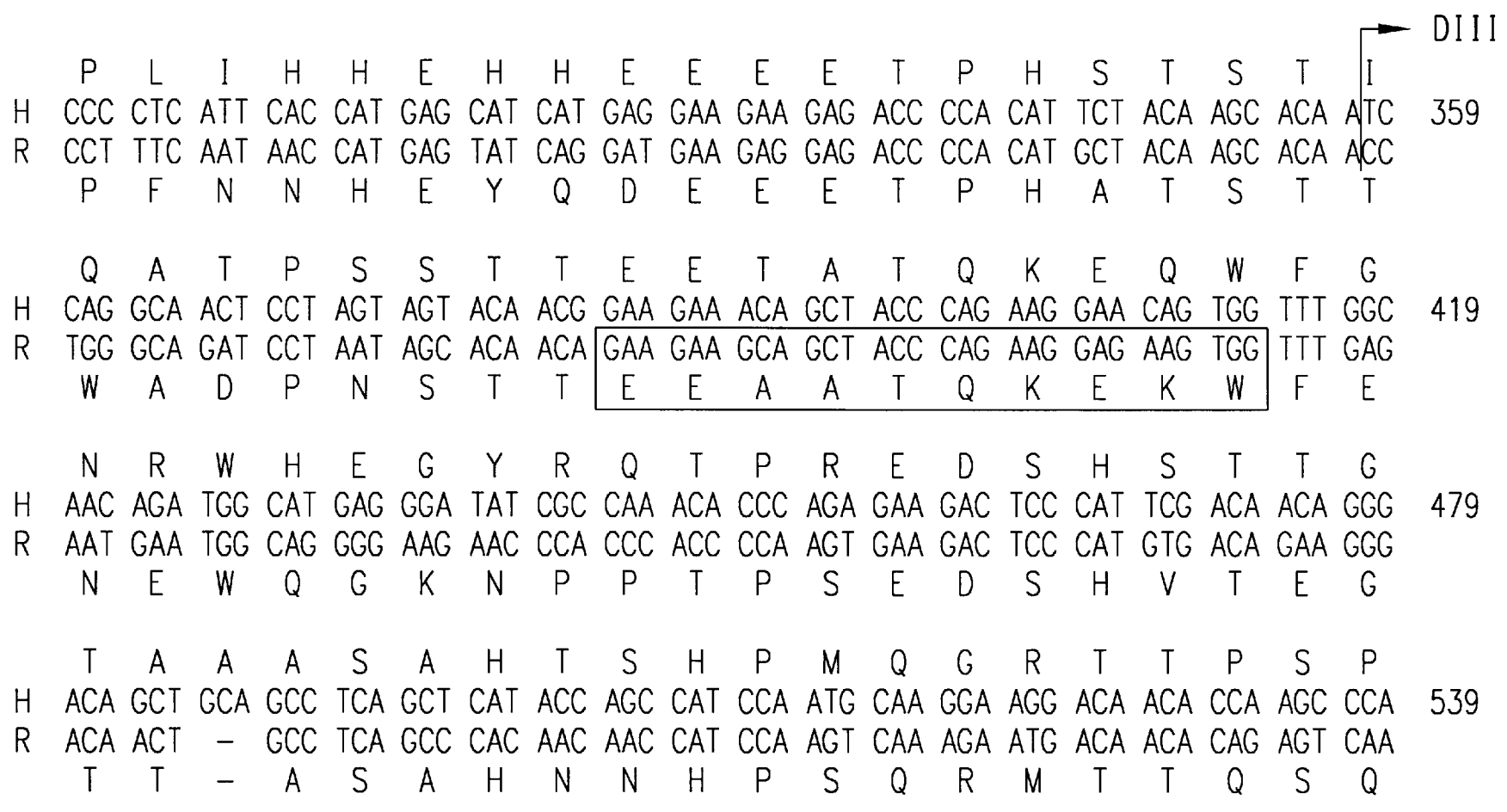
Figure 4E:
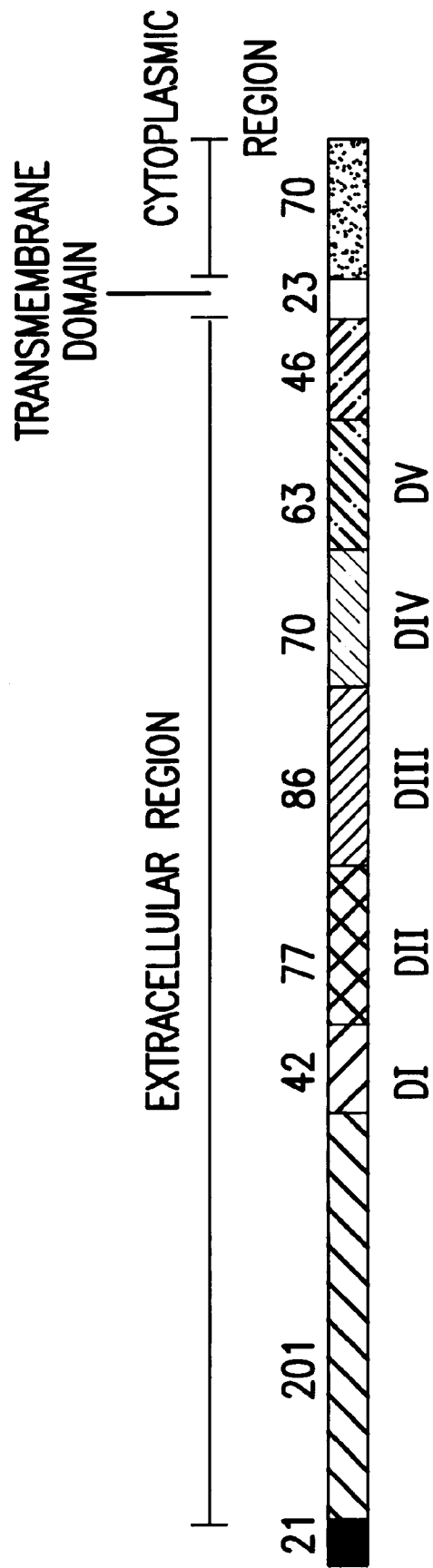
FIG. 4A: DNA and amino acid sequence of the vCD44 region of the cell line LCLC97 in man. As a comparison the DNA and amino acid sequence of the rat tumor cell line BSpASML is given, derived from the DNA sequence. The arrows indicate the limits of the five exons or domains D I to D V. H=human, R=rat. The epitope which is recognized by the monoclonal antibody 1.1ASML is boxed.
FIG. 4B: Schematic representation of the five exons (domains) D I to D V inside the extracellular region of LCLC97. Numerical data=number of amino acids.

The term vCD44 or, synonymously therewith, variant extracellular domains or regions of CD44 or sCD44, for the purposes of the present invention, on the subject of nucleic acids, denote any RNA, DNA or transcript thereof coding for one or more vCD44 proteins or domains, including those which are modified by mutations, e.g. by deletions, insertions, substitutions, inversions, transitions and transversions and those which hybridize with the DNA sequence shown in FIG. 4A under the known conventional conditions, the complementary coding strands of which code for a protein which imparts metastasizing properties to tumors, irrespective of whether these nucleic acids have been prepared and isolated conventionally by means of cell cultures or by DNA recombination, using synthetic or semisynthetic methods.

The term vCD44 or, synonymously therewith, variant extracellular domains or regions of CD44 or sCD44, when discussing a corresponding surface protein, are intended, for the purposes of the present invention, to denote all those glycoproteins originating from animals or humans which, irrespective of their preparation or isolation using conventional cell cultures or by DNA recombination or by synthetic or semisynthetic methods, occur as an additional section inside sCD44 and impart metastasizing properties to a tumor.

The term antibodies denotes mono- or polyvalent antibodies and poly- and monoclonal antibodies, and also those which are fragments and derivatives thereof, including the F(ab')$_2$, Fab' and Fab fragments, and also chimeric antibodies, hybrid antibodies having at least two antigen or epitope binding sites, single polypeptide chain antibodies, or bispecific recombinant antibodies (e.g. quadromes, triomes), interspecies hybrid antibodies, anti-idiotypic antibodies and those which have been chemically modified and must be regarded as derivatives of these antibodies and which may be prepared either by the known conventional methods of antibody production or by DNA recombination, using hybridoma techniques or antibody engineering or synthetically or semisynthetically in known manner and which have neutralizing or binding properties with respect to the vCD44 described and defined above. From the extensive literature reference is made by way of example to the work by Köhler, G. & Milstein, C., *Nature* 256:495–497 (1975); Biocca, S. et al., *EMBO J.* 9:101–108 (1990); Bird, R. E. et al., *Science* 242:423–426 (1988); Boss, M. A. et al., *Nucl. Acids Res.* 12:3791–3806 (1984); Boulianne, G. L. et al., *Nature* 312:643–446 (1984); Bukovsky, J. & Kennett, R. H., *Hybridoma* 6:219–228 (1987); Diano, M. et al., *Anal. Biochem.* 166:223–229 (1987); Huston J. S. et al., *Proc. Natl. Acad. Sd. USA* 85:5879–5883 (1988); Jones, P. T. et al., *Nature* 321:522–525 (1986); Langone, J. J. & Vunakis, H. V. (Editor), *Methods Enzymol.* 121, Academic Press, London (1987); Morrison, S. et al., *Proc. Natl. Acad. Sci. USA* 81:6851–6855 (1984); Oi, V. T. & Morrison, S. L., *BioTechniques* 4:214–221 (1986); Riechmann, L. et al., *Nature* 332:323–327 (1988); Tramontano, A. et al., *Proc. Natl. Acad. Sci. USA* 83:6736–6740 (1986); Wood, C. R. et al., *Nature* 314:446–449(1985); and Ladner, U.S. Pat. No. 4,946,778, issued Aug. 7, 1990.

With regard to the preparation of polyclonal antibodies against epitopes of vCD44 there are a number of methods available. For example, various animals may be immunized for this purpose in known manner by injecting them with vCD44, which may be of natural origin or obtained by DNA recombination or synthetic methods, or fragments thereof and the desired polyclonal antibodies are obtained from the resulting sera and purified by known methods. Alternatively, intact cells may also be used. Various adjuvants may also be used for increasing the immune response to the administration of vCD44, depending on the animal selected for immunization. Examples of these adjuvants include Freund's adjuvant, mineral gels such as aluminum hydroxide, surfactant substances such as polyanions, peptides, oil emulsions, haemocyanins, dinitrophenol or lysolecithin.

The monoclonal antibodies against an epitope of vCD44, which are preferred for use according to the invention, may be prepared by any of the techniques available for preparing antibodies by cultivating cell lines. These known techniques include, for example, the methods described by Köhler, G. & Milstein, C. (1975), loc. cit., or by Taggart & Samloff, *Science* 219:1228–1230 (1983), using hybridoma cells or the methods using human B cell hybridomas (Kozbor et al., *Immunology Today* 4:72–79 (1983)). Chimeric antibodies against vCD44 may, for example, be put together from a mouse antigen binding domain and human constant regions (Morrison et al., *Proc. Natl. Acad. Sci. USA* 81:6851–6855 (1984); Takeda et al., *Nature* 314:452–454 (1985)).

The antibodies may be purified by known methods, e.g. by immunoabsorption or immunoaffinity chromatography, by HPLC (High Performance Liquid Chromatography) or combinations thereof. Antibody fragments which contain the idiotype of the molecule may also be prepared by known methods. For example, F(ab')$_2$ fragments may be obtained by pepsin digestion of the complete poly- or monoclonal antibody. Fab' fragments may be obtained by reducing the disulfide bridges of the associated Fab'$_2$ fragment, for example, and Fab fragments may be obtained, for example, by treating the antibody molecules with papain and a reducing agent.

Any known process may be used for identifying and selecting antibodies, fragments or derivatives thereof which react with an epitope of vCD44. The process may, for example, be based on the fact that these antibodies are detectable after suitable labelling when they are bound to S isolated or purified vCD44 or by immunoprecipitation of the vCD44 purified by means of polyacrylamide gels, for example, or by the fact that antibodies against vCD44 compete with other vCD44 antibodies for binding to vCD44.

However, the present invention also relates to the use of hybridoma cell lines for preparing the antibodies or a preparation for use according to the invention and a method of producing a preparation for the use according to the invention.

For further details regarding the general use of monoclonal antibodies for immunosuppression and in autoimmune diseases, of hybrid antibodies for therapeutic purposes and antibodies produced by DNA recombination, reference is made to *Progress in Allergy*, Vol. 45, "Monoclonal Antibody Therapy" (1988) and the work of Seaman, W. E., et al., *Ann. Rev. Med.* 39:231–241 (1988).

The additional domain in vCD44 both in animals (e.g. rats) and in humans has been fully disclosed in terms of the substance parameters (DNA and amino acid sequence, location within the complete gene coding for CD44) and the preparation thereof, thus enabling the person of ordinary skill in the art, provided with this disclosure, to prepare any desired antibodies or monoclonal antibodies in accordance with the above definitions for each epitope located on this additional extracellular domain of vCD44 and to use it according to the invention so that its use is not restricted to certain specific antibodies or the hybrid cell lines which produce them. For example, the epitope recognized by mAb 1.1ASML is precisely defined by the amino acid sequence E-E-A-A-T-Q-K-E-K-W or Glu Glu Ala Ala Thr Gln Lys Glu Lys Trp (FIG. 4A).

The use of these antibodies, fragments and derivatives thereof for immunosuppression is not described in the prior art.

According to the invention, preparations with antibodies of this kind are used in immunoregulatory disorders and diseases in animals and humans, for the prevention or prophylaxis, control, diagnosis or treatment thereof.

Figure 1:
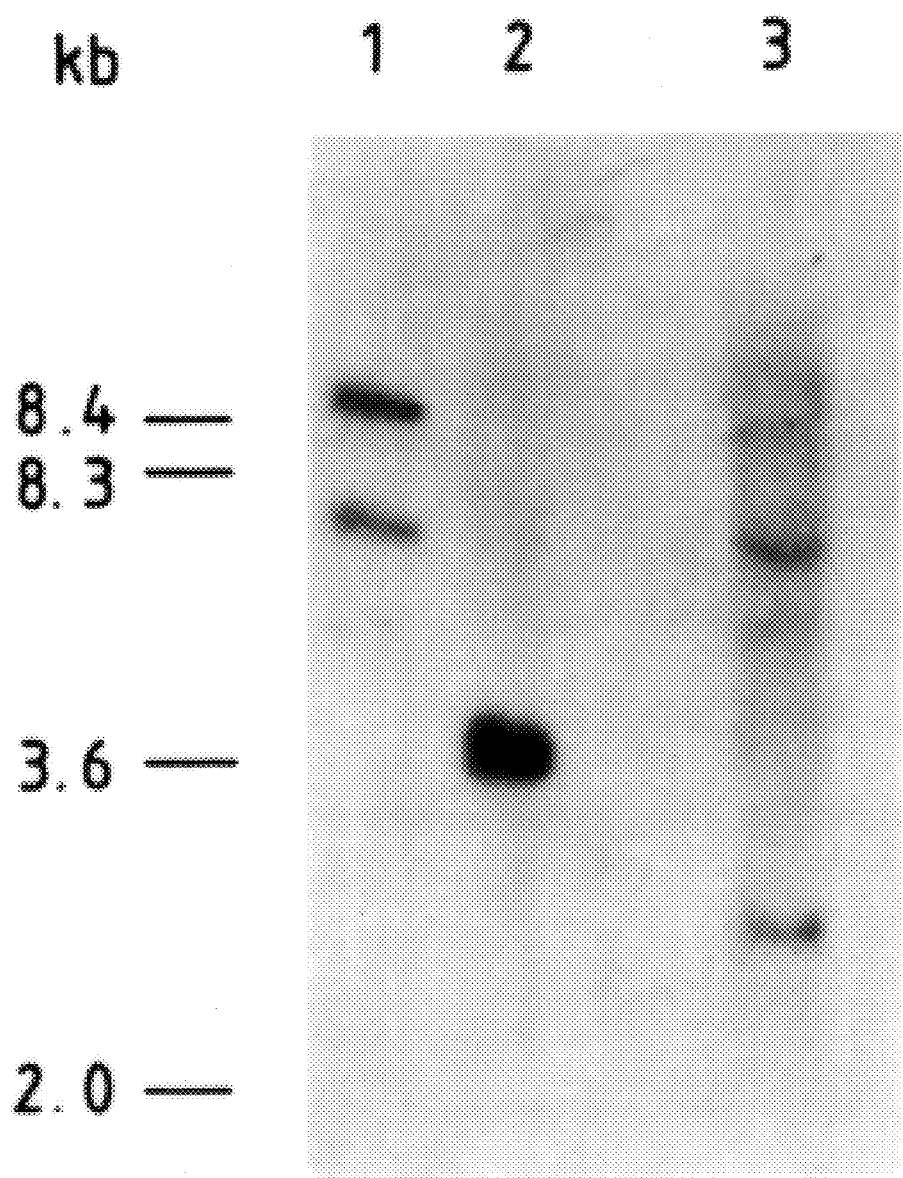
FIG. 1: Cross hybridization of vCD44 sequences between rat, mouse and man. Lane 1=rat (liver cells), lane 2=mouse (L-cells), lane 3=men (breast cancer cell line T47D)

In view of their immunosuppressant activity, the designated antibodies or preparations containing them are suitable for preventing and treating diseases and conditions which require a temporary or permanent reduction or suppression of an immune response. In particular, their use extends to suppressing the activation of the proliferation of lymphocytes or cytotoxic T-cells and/or immunocytes, e.g. for preventing or treating autoimmune diseases such as diseases of the rheumatic type, multiple sclerosis, psoriasis, atopic dermatitis, or for preventing the rejection of transplanted tissues or organs such as kidneys, heart, lungs, bone marrow, spleen, skin or cornea, in undesirable reactions during or after transfusions, allergic diseases, particularly those which affect the gastrointestinal tract and which may take the form of an inflammation, or inflammatory, proliferative and hyperproliferative diseases and cutaneous manifestations of immunological disorders such as eczematous dermatitis, urticaria, vasculitis and scleroderma.

The use according to the invention is based on the unexpected observation that an antibody directed against the variant part of CD44 (vCD44) greatly reduced the T-cell-dependent and T-cell-independent immune response in vio and in vitro. Owing to the fact that one or more of the antibodies, fragments or derivatives thereof described above neutralize the activity of vCD44, which is assumed to be necessary not only for the humoral immune response but also for the activity of proliferation and cytotoxic T-cells, the use of these antibodies according to the invention makes it possible to suppress immune response in a targeted manner which is controllable in terms of intensity and duration, depending on the quantity, duration and nature of the antibody preparation to be administered. Thus, it is particularly advantageous to use these antibodies clinically for the disorders, diseases and conditions described above, i.e. when it is desirable to achieve immunosuppression in an animal or human body.

Depending on the nature and cause of the disease or disorder to be treated or the condition which is to be influenced in an animal or human body, it may be desirable to administer the antibody preparation systemically, locally or topically to the tissue or organ in question. Systemic action is desirable, for example, when various organs or organ systems are in need of treatment, as is the case for example in systemic autoimmune diseases or allergies or in transplants of large, foreign organs or tissues. By contrast, a local effect would be considered if only local manifestations of an immunological occurrence had to be treated, e.g. in small transplants of skin or cornea or in cases of local dermatitis.

The antibodies in question may be administered by any enteral or parenteral route known to those skilled in the art. For systemic administration, for example, the substances may be administered by intravenous, intravascular, intramuscular, intraarterial, intraperitoneal, oral or intrathecal route. Rather more local administration may be achieved by subcutaneous, intracutaneous, intracardial, intralobal, intramedullar or intrapulmonary route or into the tissue to be treated (connective, bone, muscle, nerve, epithelial or bone tissue). Depending on the duration and intensity of the immunosuppressant activity required, the antibody preparations may be given one or more times a day, as well as intermittently, over a period of several days, weeks or months and in various dosages. In order to prepare an antibody preparation suitable for the forms of administration described, the injectable, physiologically acceptable solutions known to those skilled in the art may be used in sterile form. A solution for parenteral injection or infusion may be prepared using the known aqueous isotonic solutions, e.g. saline or a corresponding plasma protein solution without gammaglobulin. However, the preparation may also take the form of a lyophilized or dry preparation which can be reconstituted under sterile conditions immediately before use with one of the known injectable solutions, e.g. in the form of a kit of parts. In order to obtain the antibody preparation in its ready to use form for injection, infusion or perfusion, antibodies purified by known methods, according to the definitions given above, are mixed with one of the physiologically acceptable solutions specified, which may optionally be supplemented with known carriers or adjuvants (e.g. serum albumins, dextrose, sodium bisulfite or EDTA).

The quantity of antibody to be administered depends on the nature and severity of the illness or disorder to be treated or the condition to be influenced and on the patient in question (animal or person). However, as a guide, the dosage ranges from 1 to 1000 mg, preferably 5–200 mg of the antibody per dosage unit as is conventional for other antibodies or monoclonal antibodies, administered in amounts of from 0.01 to 20 mg per day and 0.1 to 100 mg per kg of body weight per day over longer periods (days, weeks, months) to achieve the desired effects, depending on how great a degree of immunosuppression is to be achieved and over how long a time.

The present invention is described in further detail in the following non-limiting examples.

EXAMPLE 1

Characterization of vCD44 in the rat

The process and means for characterizing the vCD44 glycoprotein in the rat and the DNA sequence coding for it are fully disclosed in the publication by U. Günthert et al., *Cell* 65:13–24 (1991), and consequently reference is made specifically thereto. This publication should therefore be regarded as incorporated by reference in its entirety as a constituent part of Example 1.

EXAMPLE 2

Characterization of vCD44 in humans 2.1 Identification of homologous vCD44 sequences between the rat, the mouse and humans Genomic DNA was isolated by known methods (T. Maniatis et al., in: *Molecular Cloning, A Laboratory Manual,* Cold Spring Harbor (1982)) from rat liver, L-cells in the mouse and the human breast cancer cell line T47D (ATCC No. HTB133). 10 $\mu$g thereof were fully digested with EcoRI by standard methods and prepared for the subsequent crosshybridization with a hybridizing probe consisting of the cDNA section of positions 941–1108 of pMeta-1 of the variant CD44 region in the rat (U. Günthert et al., *Cell* 65:13–24, 1991), and prepared and filter-fixed for DNA:DNA Southern hybridization by known methods. The hybridization was carried out overnight at 65° C. in 6×SSC. The filters were then washed three times for 30 minutes at 65° C. in washing buffer (2×SSC, 0.1% SDS) and finally once in 0.5×SSC, 0.1% SDS. In human, rat and mouse DNA fragments were found which are clearly homologous with one another (FIG. 1).

2.2 Expression of vCD44 sequences in human tumor cells

Figure 2:
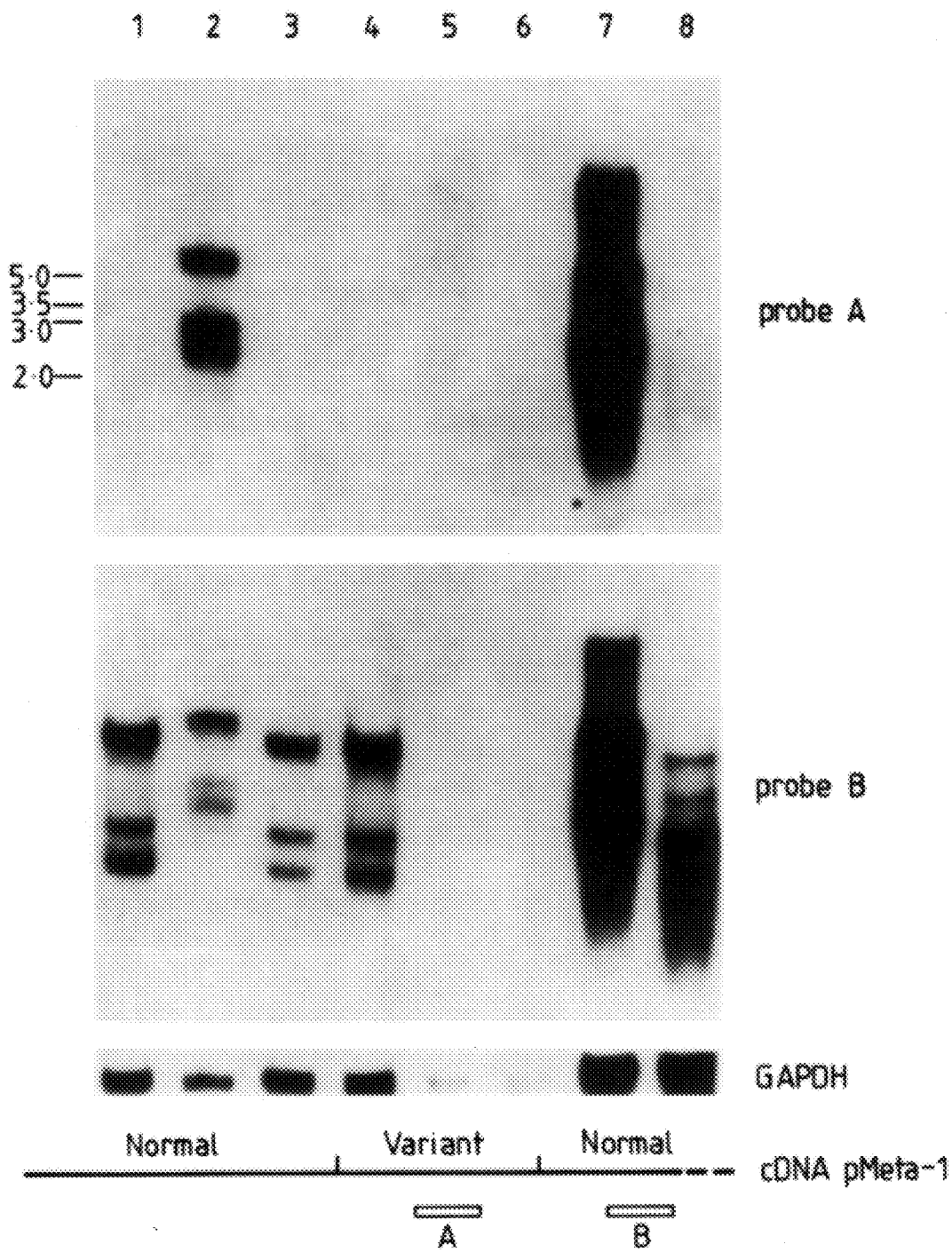
FIG. 2: Expression of vCD44 and sCD44 sequences in human tumor cell lines. Lane 1=LCLC103, lane 2=LCLC97, lane 3=CH3LC, lane 4=EPLC32M1, lane 5=SCLC24, lane 6=SCLC18. Lane 7 corresponds to the rat cell line BSp78ASML and lane 8 to the rat cell line BSp73AS. GAPDH=glycerine aldehyde phosphate dehydrogenase for determining the relative amounts of the quantities of RNA applied.

3 μg of poly(A)$^+$ RNA were prepared for RNA hybridization by Northern blotting from the known lung cancer cell lines SCLC18, SCLC24, EPLC32M1, CH3LC, LCLC97, LCLC103, for which both the culture conditions and the properties have been described (G. Bepler et al., *J. Cancer Res. and Clin. Oncol.* 113:31–40 (1987); G. Bepler et al., *Differentiation* 37:158–171 (1988); H.-H. Heidtmann et al., *Cancer Res.* 49.6960–6965 (1989)). Before the "blotting" with ethidium bromide-stained RNA in the gel it was established that equal quantities of RNA had been applied to the gel or were present on each lane. The preparation of the poly(A)$^+$ RNA, the denaturing thereof and the blotting as well as the other processes of RNA blot analysis were carried out according to U. Günthert et al. (1991), loc. cit. Probe A from the variant CD44 region of pMeta-1 used for hybridization was identical to that described under point 2.1. The region given in U. Günthert et al. (1991), loc. cit. was selected as probe B, which originates from the normal CD44 region of pMeta-1 located downstream of the vCD44. As shown in FIG. 2, the human cell line LCLC97 of a large cell lung cancer expressed sequences which are homologous to the probe A of vCD44 in the rat. With regard to probe B (normal sCD44 region in the rat) clear hybridization signals or expressions of sCD44 could also be detected in other cell lines. The cell lines SCLC18 and SCLC24 were negative for both probes. As a comparison, the RNAs from the rat cell lines BSpAS (non-metastasizing) and BSpASML (metastasizing) were applied (FIG. 2, lanes 7 and 8).

2.3 Isolation and characterization of CD44 variants in man

The poly(A)$^+$ RNAs were isolated by known methods (M. Schwab et al., *Nature* 303:497–501 (1983)) from the known cell lines SW260, HT29 (obtainable from the ATCC, Nos. CCL227 and HTB38), LCLC97 (as described in 2.2), HPKII (eratinocyte cell line described in P. Boukamp et al., *J. Cell Biol.* 106:761–771 (1988)) and MeWo (melanoma cell line T. E. Carey et al., *Proc. Natl. Acad. Sci. USA* 73:3278–3282 (1976)) and subsequently transcribed, for PCR amplification, with AMV-reverse transcriptase (20 units) into single strand DNA.

Figure 3:
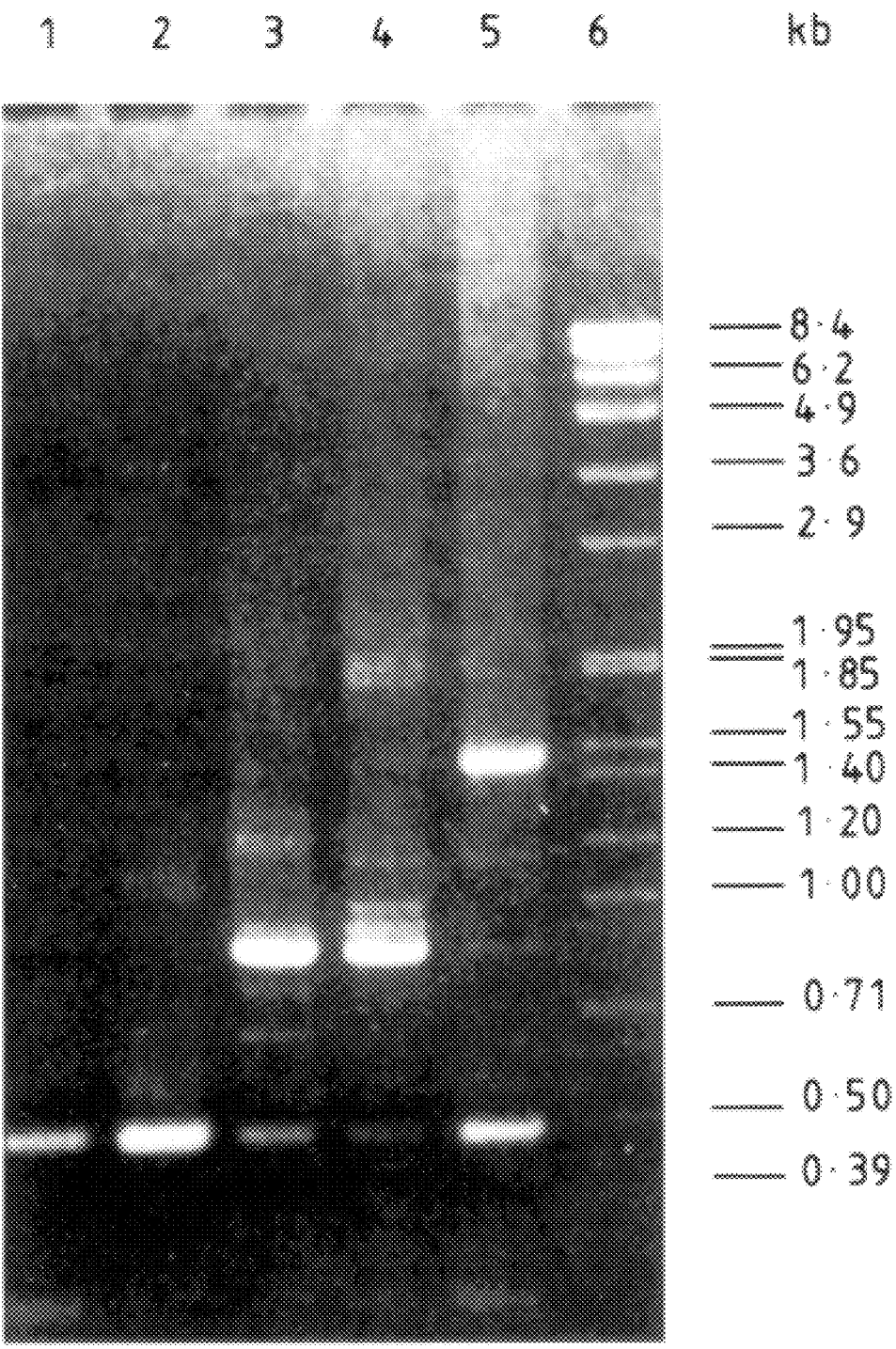
FIG. 3: Agarose gel electrophoretic separation of cDNAs obtained by PCR amplification and complementary to the CD44 RNAs expressed in various human cell lines. Lane 1–SW620, lane 2=MeWo, lane 3=HT29, lane 4=LCLC97, lane 5=HPKII, lane 6=length marker, Boehringer Mannheim, No. 7.

Preparation of the cDNAs using PCR amplification was carried out using two primers from normal human CD44 cDNA sequences and, more specifically, oligonucleotides which represent positions 513 to 540 and 900 to 922 (I. Stamenkovic et al., *Cell* 56:1057–1062 (1989)) (examples of PCR technology may be found in Mullis, U.S. Pat. No. 4,683,195; Mullis, U.S. Pat. No. 4,683,202; and PCR Protocols: *A Guide to Methods and Applications*, Innis et al. (eds.), Academic Press, Inc., San Diego, Calif. 92101 (1990)). This choice was made because the insertion of the metastasis-specific extra sequences had been found between these positions in the rat (U. Günthert et al. (1991), loc. cit.). After 60 cycles PCR was complete and the DNA products obtained were separated by known methods (T. Maniatis et al. (1982), loc. cit.) by agarose gel electrophoresis (1% agarose, Sigma) and stained with ethidium bromide. With regard to the "normal" CD44 RNA expression (sCD44), when using these primers a cDNA 440 bp long was obtained (including the restriction site for cloning), as could have been expected for the expression of this RNA (MeWo and SW620 cells). With the RNAs from the other cell lines a band of the same length was found but in addition there were larger PCR products (cDNAs). Prominent fragments with a length of 850 bp were obtained with HT29 and LCLC97 cells. In HPKII cells the strongest band, apart from the 440 bp band, was found in the region of 1.5 kb long. These findings are shown in FIG. 3.

All the cDNAs obtained from the PCR amplifications were cloned into the vector pT7T3–19 (BRL, Gibco) and then sequenced using standard methods. Clones of MeWo cells and SW60 cells contained the normal CD44 (sCD44) sequences (I. Stamenkovic et al. (1989), loc. cit.).

The DNA and amino acid sequence of the entire variant region of the longest cDNA obtained from LCLC97 cells by PCR and cloned in pT7T3–19 is shown in FIG. 4A. The variant section comprises 1014 bp (or 338 amino acids) inserted between nucleotide positions 782 and 783 of the "normal" sCD44 RNA. The sequence of this variant region is divided into five sections or domains, which is in accordance with the discovery of smaller PCR products which comprise precisely defined areas of the largest clone (from LCLC97). In view of the fact that such clones can be reproducibly isolated from various cell lines it can be inferred that these five domains D I to D V of the LCLC97 cell line (FIG. 4A) reflect five different exons which, by means of differential RNA splicing, bring forth the RNAs from which the PCR clones originate. The existence of such domains has been confirmed by the discovery of a similar state of affairs in rat tumor cell lines.

FIG. 4B shows a diagrammatic survey of the situation which obtains in LCLC97. A cDNA clone which is homologous to the longest splice product in LCLC97 cells was isolated from the metastasizing rat tumor cell line BSpASML using PCR by known methods (U. Günthert et al. (1991), loc. cit.). FIG. 4A shows a comparison of the amino acid sequence derived therefrom with that of the human clone (from LCLC97). The position of insertion of these variant sequences differs in three amino acids (amino acid position 222 in humans and position 226 in rats). Domain I shows 83%, domain II 83%, domain III 71%, domain IV 82% and domain V 66% homology relative to the corresponding amino acid sequences in the rat.

The rat cDNA corresponding to LCLC97 in FIG. 4A, which imparts metastatic potential to a tumor (U. Günthert et al. (1991), loc. cit.), comprises amino acids 258 to 420 and codes for domains II and III. The amino acid sequence in these two domains is identical to the amino acid sequence of the BSp73ASML specific domains published by U. Günthert et al. (1991), loc. cit., derived from the cDNA of the clone pMeta-1.

EXAMPLE 3

Immunosuppressant activity of the monoclonal antibody 1.1 ASML directed against vCD44

3.1 Effect of anti-vCD44 (1.1ASML) on the humoral immune response

200 μg of the monoclonal antibody 1.1ASML were injected intravenously into BDX rats at the same time as the antigen was administered. The T-cell-independent antigen administered consisted of 50 μg of 2,4,6-trinitrophenyl-lipopolysaccharide (TNP-LPS) (J. M. Fidler, *Cellul. Immunol.* 16:223 (1975)) and the T-ell dependent antigen consisted of 5×10$^8$ cells of the hapten-protein conjugate 2,4, 6trinitrophenyl horse red blood cells (TNP-HRBC) (M. B. Rittenberg, *Proc. Soc. Exp. Biol. Med.* 132:575–581 (1969)), administered by intraperitoneal route to immunize the rats. The number of antigen-specific plaque forming cells (PFC) was determined 3 and 5 days after the administration of the antigen or the injection of 1.1ASML, using as target cells conjugates of 2,4,6-trinitrophenyl with sheep erythrocytes (sheep red blood cells, TNP-SRBC) and HRBC (horse erythrocytes or horse red blood cells). The PFC were determined according to a modification (M. Zöller & G. Andrighetto, *Cellul. Immunol.* 89:310 (1984)) of the hemolytic plaque assay (N. K. Jerne & A. A. Nordin, *Science* 140:405 (1963)). The quantity of anti-TNP antibody of the serum of the immunized rats was determined by a known method (M. Zöller, *Scand. J. Immunol.* 31:619 (1990)), by comparing serum titration curves with standard curves of purified anti-TNP monoclonal antibodies using ELISA (E. Engvall & P. Perlman, *J. Immunol.* 109:129 (1982)).

The immune responses against both the T-cell independent antigen and also the T-cell dependent antigen were greatly reduced or suppressed in the presence of 1.1ASML. The number of antigen specific PFC was reduced to 8% to 21% compared with control-stimulated animals and the resulting serum-antibody level was also suppressed (Table I).

TABLE I

Effect of anti-vCD44 1.1ASML on the activation of B cells

| Antigen | mAB | PFC/10$^6$ SC* | | Serum anti-TNP (mg/ml) |
|---|---|---|---|---|
| | | anti-TNP | anti-HRBC | |
| TNP-LPS | — | 620 | | 108.0 |
| | 1.1ASML | 52 | | 6.1 |
| TNP-HRBC | — | 214 | 1582 | 5.4 |
| | 1.1ASML | 20 | 337 | 2.7 |

*SC = spleen cells

These data lead one to conclude that the antibody functions are blocked either through only inhibiting the stimulation of B-lymphocytes or that both the B- and T-lymphocytes are blocked.

However, the expression of vCD44 was necessary not only for the humoral but also for the cellular immune response.

3.2. Effect of anti-vCD44 on the activation of T-lymphocytes

The efficiency of an allogenic stimulation was measured 4 days after immunization by determining the proliferation of T-cells after renewed stimulation in vitro. The DA rats used for this purpose were treated either with only 5×10$^7$ irradiated lymphocytes (3000R) from BDX rats or with irradiated BDX lymphocytes plus 1.1ASML (200 μg). Their spleen and lymph node cells were restimulated in vitro with irradiated BDX lymphocytes. The spleens and lymph nodes were collected 5 days later. The organs were carefully crushed and after washing in 15 ml RPMI 1640 the cells were adjusted to 3×10$^6$ cells/ml RPMI1640, supplemented with L-glutamine (4 mM), antibiotics (34 μM penicillin, 32 μM streptomycin), 5×10$^{-5}$M 2-mercaptoethanol, 10$^{-3}$M HEPES buffer and 2% heat-inactivated rat serum (RPMI-s).

Aliquots of the cell suspension were titrated three times in microtiter plates having U-shaped wells. In each well were placed 1.5×10$^{-5}$ irradiated (3000R) BDX lymphocytes in 100 μl of RPMI-s and, optionally, in a final concentration of 10 μg/1 ml RPMI-s, monoclonal antibodies 1.1ASML purified by protein A sepharose 4B chromatography (Pharmacia). The cultures were incubated for 72 hours at 37° C. with 5% $CO_2$ gas added to the atmosphere. The proliferation of the DA lymphocytes was determined by the addition of 50 μCi $^3$H-thymidine in the course of the last 8 hours of cultivation.

The incorporation of $^3$H-thymidine as a measurement of the proliferation of T-cells and spleen cells from those rats which had been allogenically immunized together with 1.1ASML, was drastically reduced by comparison with the cells of rats which had been immunized in the absence of this antibody. This result still stood, regardless of whether spleen cells and lymph node cells had been restimulated with allogenic cells on their own or with allogenic cells plus 1.1ASML (FIG. 5).

3.3 Influence of anti-vCD44 on the activation of cytotoxic T-cells

Compared with the T-cell proliferation in Example 3.2 the cytoxic activity was determined after the seventh day of allogenic stimulation. With regard to the need for vCD44 during the maturation and/or activation of cytotoxic T-cells (CTL) a virtually identical image to that obtained in Example 3.2 was achieved (FIG. 5). In the presence of 1.1ASML the number of cytotoxic T-lymphocytes was dramatically reduced (FIG. 6).

Spleen cells from DA rats (DA spleen cells) which had been immunized with BDX lymphocytes as described in Example 3.2 were collected 7 days after immunization and tested for cytotoxic activity against BDX lymphoblasts (primary CTL).

DA spleen cells obtained immediately after immunization were adjusted to 1×10$^7$ cells/ml RPMI-s. Aliquots of the cell suspension (effector cells, E) were titrated in microtiter plates having U-shaped wells and 100 μl of target cells (target cells, T, 1×10$^4$ $^{51}$Cr-labelled BDX concanavalin A lymphoblasts) were added thereto. After 6 hours incubation at 37° C. the plates were centrifuged, aliquots of the supernatants were removed and the radioactive radiation of the $^{51}$Cr was measured in a γ-counter. FIG. 6 shows the mean percentage of specific radioactivity taken as the average of three values.

All publications mentioned hereinabove are hereby incorporated by reference in their entirety.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A method of reducing or suppressing an immune response in a mammal, comprising administering to said mammal an effective amount of an antibody, or a fragment or domain of said antibody that binds an epitope of variant CD44, said epitope being comprised within SEQ ID NO:2; or SEQ ID NO:4, such that said immune response is reduced or suppressed.

2. The method according to claim 1, wherein said antibody is a monoclonal antibody.

3. The method according to claim 1, wherein said antibody is selected from the group consisting of a chimeric antibody having an antigen binding domain of a mouse antibody and a constant region domain of a human antibody, a hybrid antibody, an anti-idiotypic antibody, a single-chain polypeptide antibody and a bispecific antibody.

4. The method of claim 1, wherein said epitope of variant CD44 comprised within SEQ ID NO:4, and is further comprised within SEQ ID NO:5.

5. The method according to claim 4, wherein said antibody is a monoclonal antibody.

6. The method according to claim 4, wherein said antibody is selected from the group consisting of a chimeric antibody having an antigen binding domain of a mouse antibody and a constant region domain of a human antibody, a hybrid antibody, an anti-idiotypic antibody, a single-chain polypeptide antibody and a bispecific antibody.

* * * * *

UNITED STATES PATENT AND TRADEMARK OFFICE
CERTIFICATE OF CORRECTION

PATENT NO.  : 5,951,982
DATED       : September 14, 1999
INVENTOR(S) : Margot Zoller, Peter Herrlich and Helmut Ponta It is certified that error appears in the above-identified patent and that said Letters Patent is hereby corrected as shown below:

On title page, item [73] should read as follows:

Kernforschungszentrum Karlsruhe
W-7500 Karlsruhe 1
Germany

Deutsches Krebsforschungsz Heidelberg
W-6900 Heidelberg
Germany

Boerhinger Ingelheim International GmbH
W-6507 Ingelheim
Germany

Signed and Sealed this

Twenty-first Day of March, 2000

Attest:

Attesting Officer

Q. TODD DICKINSON

Commissioner of Patents and Trademarks